United States Patent [19]
Lingenhöle et al.

[11] Patent Number: 5,782,634
[45] Date of Patent: Jul. 21, 1998

[54] MEDICAL, IN PARTICULAR DENTAL TURBINE HANDPIECE

[75] Inventors: Bernhard Lingenhöle, Warthausen-Birkenhard; Eugen Mohr, Ummendorf, both of Germany

[73] Assignee: Kaltenbach & Voigt GmbH & Co., Biberach, Germany

[21] Appl. No.: 695,855

[22] Filed: Aug. 9, 1996

[30] Foreign Application Priority Data

Aug. 11, 1995 [DE] Germany .................. 195 29 668.0

[51] Int. Cl.⁶ .................. A61C 1/05; A61C 1/08
[52] U.S. Cl. .................. 433/132; 415/904
[58] Field of Search .................. 433/114, 115, 433/132; 415/904

[56] References Cited

U.S. PATENT DOCUMENTS

| | | |
|---|---|---|
| 3,567,330 | 3/1971 | Apelskog et al. .................. 433/132 |
| 3,708,240 | 1/1973 | Theis, Jr. et al. .................. 433/132 |
| 3,865,505 | 2/1975 | Flatland . |
| 5,374,189 | 12/1994 | Mendoza .................. 433/132 |
| 5,407,352 | 4/1995 | Kawata .................. 433/132 |
| 5,464,350 | 11/1995 | Bierbaum .................. 433/114 |
| 5,567,154 | 10/1996 | Wohlgemuth .................. 433/132 |

FOREIGN PATENT DOCUMENTS 6-98898   4/1994   Japan .................. 433/132

*Primary Examiner*—Ralph A. Lewis
*Attorney, Agent, or Firm*—Scully, Scott, Murphy & Presser

[57] ABSTRACT

In a medical, in particular dental turbine handpiece, having a supply line (8) and a discharge line (9) for the turbine compressed air, whereby a valve (12) is arranged in one line, which valve is controllable by a pneumatic parameter in the other line, the valve (12) is arranged in the discharge line (9) and is so controllable that it closes when a limit value of the parameter in the supply line (8) falls below a minimum value.

10 Claims, 2 Drawing Sheets

MEDICAL, IN PARTICULAR DENTAL TURBINE HANDPIECE

BACKGROUND OF THE INVENTION

1. Field of the Invention

The invention relates to a turbine handpiece with the preamble of claim 1, utilized for medical or dental purposes, including a supply line and a discharge line for turbine compressed air, whereby a valve is arranged in one line, with the valve being controllable responsive to a pneumatic parameter set in the other line.

2. Discussion of the Prior Art

A turbine handpiece of this kind is described in U.S. Pat. No. 3,865,505. With this known turbine handpiece, the valve is arranged in the supplying line section and it is so controlled, by means of an adjustment device in dependence upon the pressure prevailing in the discharging line section or upon the flow speed contained therein, that it is increasingly opened with decreasing pressure or with decreasing flow speed and with increasing pressure and increasing flow speed is decreasingly closed. By these means, a speed-of-rotation controller is provided for the speed of rotation of the treatment tool.

With a turbine drive of the present kind, when the turbine wheel is switched off, there occurs a running down of the turbine wheel, which is the result of the stored rotational momentum in the drive. During this running down, the turbine wheel presses or pumps air in the discharging line section so that in the chamber in which the turbine wheel is located a partial vacuum arises which seeks to fill itself by means of sucking in of air through the annular gap present between the drive shaft and the housing. This suction air flow encourages the penetration of contaminants and/or liquid into the turbine chamber. This is undesired because this may contain contaminants of infectious agents from the mouth of the patient, which upon the treatment of the next patient could issue from the turbine handpiece and contaminate this patient.

SUMMARY OF THE INVENTION

The object of the invention is to so configure a turbine handpiece of the kind described herein above, in which the suction effect is substantially reduced or avoided.

In the configuration in accordance with the invention, the discharge line is so controlled by means of the valve, in dependence upon the pneumatic parameter contained in the other line, that upon a switching on of the compressed air supply the discharge line is opened and upon a switching off is closed. As a consequence, the turbine wheel running down cannot drive air into the discharge line and therefore there can arise in the internal chamber containing the turbine wheel neither a partial vacuum nor a suction flow.

The configuration in accordance with the invention is advantageous not only for the reasons given above, but it is also of simpler and more compact, and reliably functioning, structure of longer working life, which can be economically manufactured and assembled.

BRIEF DESCRIPTION OF THE DRAWINGS

Below, the invention and further advantages which can be achieved thereby will be explained in more detail with reference to exemplary embodiments and the drawings, which show.

DETAILED DESCRIPTION OF PREFERRED EMBODIMENTS

Figure 1:
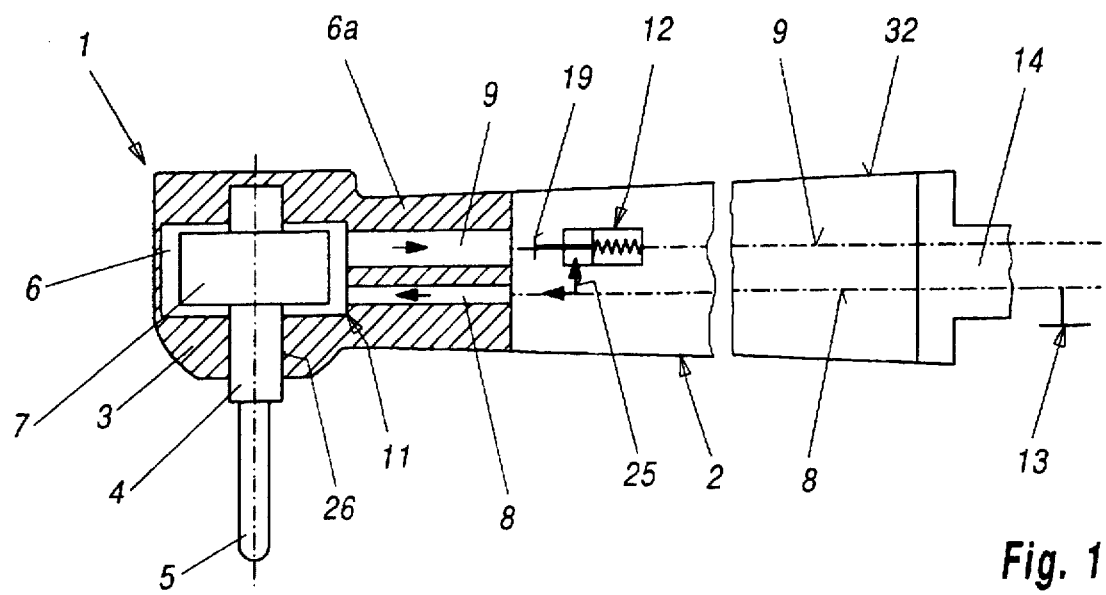
FIG. 1 a dental treatment instrument configured in accordance with the invention, in the form of an angled handpiece, in vertical section, partially in only schematic or outline representation.

The main parts of the medical, in particular dental treatment instrument, generally designated by 1, are a handpiece 2 with a so-called angled head 3, a drive shaft 4 rotatably mounted in the angled head 3, which shaft penetrates through the wall of the angled head 3 to the outside and with which there can be coaxially connected a treatment tool 5, by means of a suitable mounting device not shown in detail, a turbine wheel 7 mounted rotatably with the drive shaft 4 in a chamber 6 of the angled head 3, which turbine wheel—with a supply line 8 for compressed air, extending longitudinally through the handpiece 2 into the chamber 6 at a suitable position, and a discharge line 9 extending oppositely—forms a compressed air turbine 11, and a valve 12 for closing the discharge line 9 when the compressed air supply through the supply line 8 is switched off. The latter can be effected by the actuation of a schematically indicated valve 13, which for hand operation may be arranged in the region of the handpiece 2 and for foot operation may be arranged in the floor region of an associated treatment chair. The discharge line 9 extends from an outlet opening 10 in a middle position in the peripheral wall 6a of the chamber 6.

The rear end region of the treatment instrument 1 or handpiece 2 is represented only in a simplified manner. In the rear end region, a flexible supply line 14 is connected to the handpiece 2, which supply line extends from a supply device for a dental treatment station.

As can be understood from the Figures, the valve 12 is arranged in the discharge line 9 and it is formed in the manner of a pneumatic cylinder having a small housing 16 in which a piston disk 17 and a piston rod 18 connected therewith are guided coaxially displaceably, whereby the piston rod 18 carries a closure member 19 at its free end and is biased by means of a spring 20 with the closure member 19 against a valve opening 21 of the discharge line 9.

In the present embodiment, in which the valve 12 is arranged in the discharge line 9, there is present a stepped widening of the discharge line 9, widening in the direction of the return, at a spacing to the rear from an annular shoulder surface 22 such that the closure member 19—under the effect of the forwardly directed tension of the spring 20—closes the valve opening 21 in its forward thrust position. The piston 17 automatically takes up this position upon a switching off of the compressed air supply by means of the valve 13. The spring 20 is preferably arranged in the rear chamber 24a of the cylinder housing 16. The forward chamber 24b is permanently connected with the supply line 8 by means of a connection line 25.

During the compressed air action on the turbine 11 the compressed air arrives in the forward chamber 24b of the cylinder housing 16 through the connection line 25, whereby the piston 17 is pressed into its rearward position against the force of the spring 20, in which rearward position closure member 19 opens the valve opening 21, whereby the spent air of the turbine 11 is discharged through the discharge line 9.

It is to be noted that with regard to the plane of the drawing in FIG. 1, in front of and behind the valve housing 16 in each case there is present a sufficiently large free cross-section of the discharge line 9 such that the compressed air discharge due to the presence of the cylinder housing 16 in the discharge line 9 hardly affects the spent air discharge.

Figure 3:
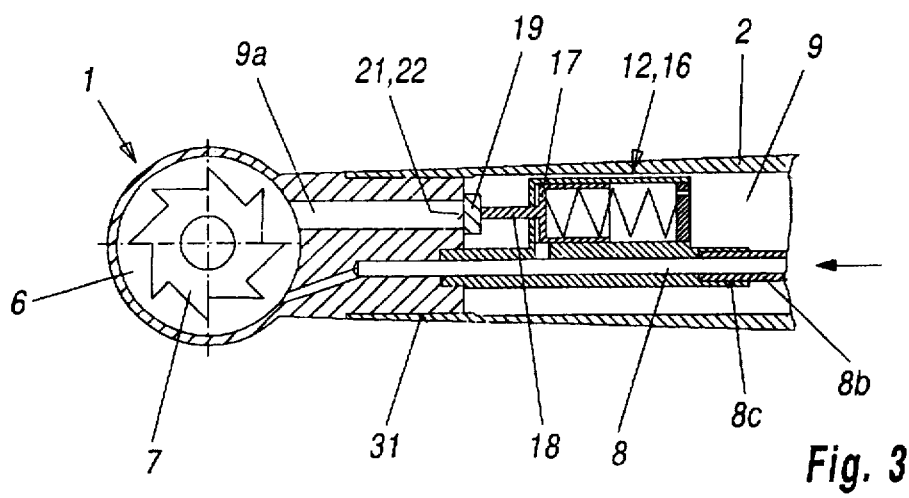
FIG. 3 the angled handpiece according to FIG. 2 in another functional representation.

As soon as the compressed air supply is switched off with the valve 13, the spring 20 automatically displaces the piston rod 18 with the closure member 19 into the closed position in accordance with FIG. 3. Thus, during the running down of the turbine wheel 7, rotating with a high speed of rotation, no air can be pumped out of the chamber 6 into the discharge line 9. As a consequence, neither can the running down of the turbine wheel 11 generate a partial vacuum in the chamber 6 and therefore there is no suction of air in the region of the bearing gap 26, on the tool side of the drive shaft 4. As a consequence, neither are any contaminants sucked into the bearing gap 26 or into the chamber 6.

Figure 2:
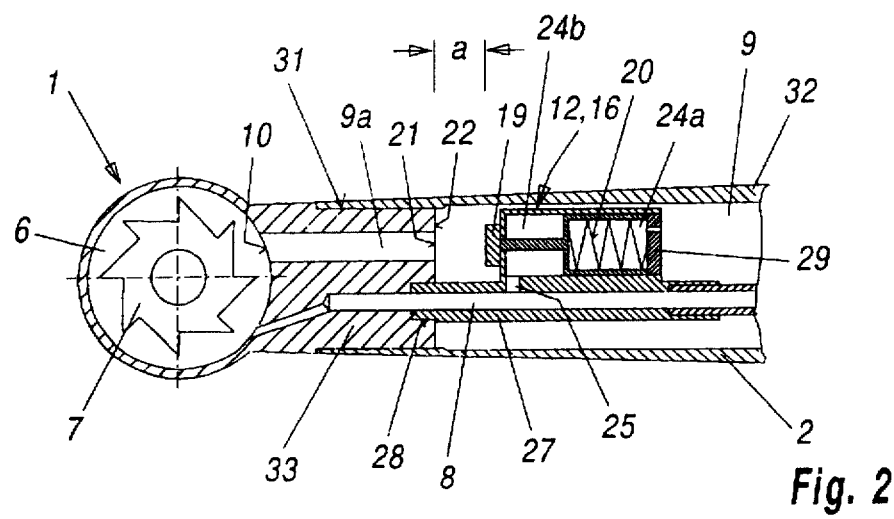
FIG. 2 the angled handpiece according to FIG. 1, in horizontal section and in a view from above.

As can be clearly understood from FIGS. 2 and 3, the cylinder housing 16 is arranged on a pipe piece 27 forming a section of the supply line 8, which pipe piece is sealingly inserted in a bore widening 28 at the rear end of the angled head 3. Thereby, the pipe piece 27, forming a structural unit with the cylinder housing 16, is secured against rotation around its longitudinal middle axis by means of bounding surfaces which are not illustrated. Because of this configuration, no particular positioning of the cylinder housing 16 is need. Because of the predetermined spacing of the piston rod 18, arranged coaxially with the discharge line section 9a in the angled head 3, the position of the piston rod is ensured by means of the mounting of the pipe piece 27. A particular mounting is not needed for the cylinder housing 16.

As can further be understood from FIGS. 2 and 3, the cylinder housing 16 may be formed in one piece with the pipe piece 27 or may be formed thereon. The common cylinder chamber of the cylinder housing 16 is closed to the rear by means of an inserted closure wall 29 which has a venting opening.

To the rear, there may be arranged on the pipe piece 27 a further supply line section 8b, by means of a plug-in socket connection 8c.

The angled head 3 is connected with a grip sleeve 32 of the handpiece 2 by means of a plug-in connection 31, whereby the grip sleeve 32 sealingly engages over a rear plug-in pin 33 of the angled head 3 and is e.g. fixedly connected by means of a press seating or screwing.

Figure 4:
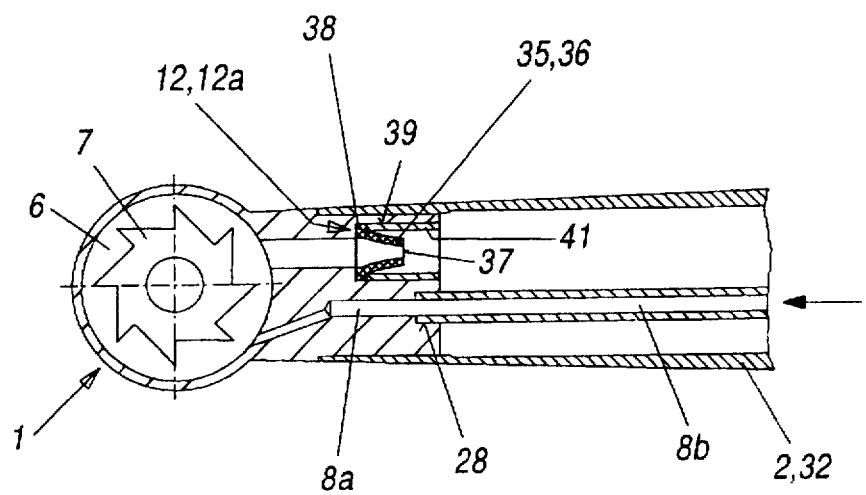
FIG. 4 a handpiece in horizontal section in a view from above, and with modified configuration of a valve.
Figure 5:
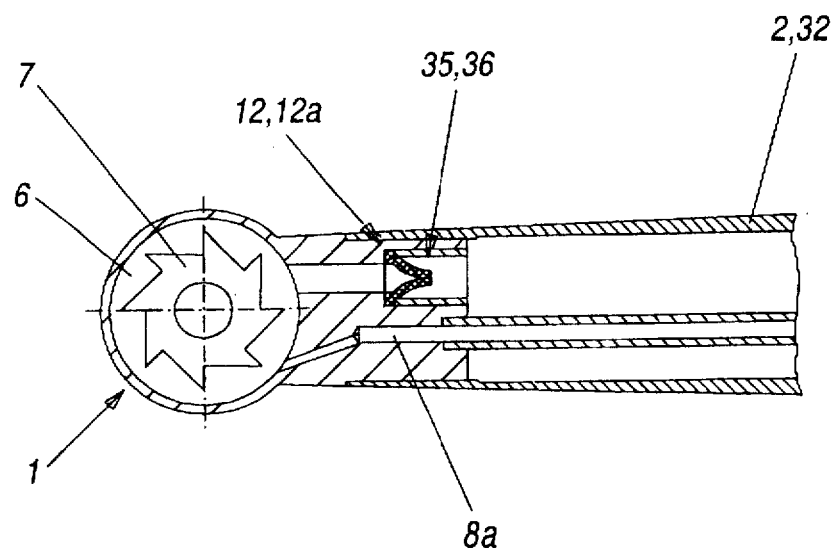
FIG. 5 the handpiece according to FIG. 4 in the closed condition of the valve.

With the exemplary embodiment according to FIGS. 4 and 5, a modified, simplified valve 12 is employed. Here, a so-called lip valve 12a is involved, which has one or more lips 35 which are part of a mouth wall 36 closed in the circumferential direction and which are—because of an internal elasticity—so biased one against another that they bear on one another sealingly and close the valve opening 37 which they surround. The mouth wall 36 converges from a preferably circular foot flange 38 which is inserted appropriately in a channel widening 39 of the discharge line section 9a running in the angled head 3. For axially fixing the foot flange 38, a sleeve 41 is fixedly inserted in the preferably circular channel broadening 39, e.g. clamped in place or glued in place.

In functional operation of the turbine 11, the lip valve 12a is opened by means of the return pressure of the exhaust air in the discharge line 9, as shown in FIG. 4. After the switching off of the compressed air supply by means of the valve 13, the lip valve 12a automatically takes up its closed position whereby the discharge line 9 is closed and likewise no air can be pumped on into the discharge line 9 out of the chamber 6 by means of the running down turbine wheel 7. As a consequence, also with this exemplary embodiment, no partial vacuum can arise in the chamber 6 upon running down of the turbine wheel 7, and thus no suction of air in the mounting gap 26 can take place.

The lip valve 12a is preferably of a suitable plastics which is able to provide the elasticity of the lips 35 and which makes possible a manufacture of the lip valve body in one piece.

The pipe piece 27 and the cylinder housing 16 with the piston disk 17, the piston rod 18 and the closure member 19 as well as the closure wall 29, may be of metal or also plastics.

In the configuration according to FIGS. 4 and 5, the section 8b of the supply line 8 running in the grip sleeve 32 is formed by means of a small pipe or a hose, which is inserted fixedly and sealingly in bore widening 28.

In FIG. 1, for reasons of clarity, the supply line 8 and the discharge line 9 are arranged one above another. This configuration is capable of functioning, but it is more advantageous to arrange the lines 8, 9 in one plane, preferably in the middle plane of the turbine wheel 7, as is shown in FIGS. 2 to 5.

We claim:

1. A turbine handpiece for medical and dental applications; comprising a turbine chamber (6) in said handpiece; a turbine wheel (7) being rotatably mounted in said turbine chamber; a supply line (8) for pressurized air communicating with said turbine chamber; a discharge line (9) for outgoing air communicating with said turbine chamber; a valve (12) being arranged to automatically prevent a flow of outgoing air in said discharge line; and a connecting line (25) for connecting said valve (12) with the supply line (8), said valve being maintained in an open position responsive to pressure reigning in said supply line (8) and closing upon said pressure falling below a predetermined minimum value.

2. Turbine handpiece according to claim 1, wherein said valve (12) comprises a closure member (19); and biasing means (2) for imparting a spring force to urge said closure member into a closed position.

3. Turbine handpiece according to claim 1, wherein said valve (12) comprises a cylinder-piston unit (16).

4. Turbine handpiece according to claim 1, wherein said valve (12) is arranged downwardly in the direction of flow of an opening with which the discharge line (9) is connected with the turbine chamber (6).

5. Turbine handpiece according to claim 4, wherein said valve (12) is arranged downwardly in the direction of flow of a stepped surface (22) of said discharge line (9) which widens in cross-section in the direction of flow of the air.

6. Turbine handpiece according to claim 1, wherein said valve (12) is arranged on a wall portion or pipe section (27) containing the supply line (8).

7. Turbine handpiece according to claim 6, wherein said connecting line (25) is formed by a hole in the structure of said wall portion or pipe section (27).

8. Turbine handpiece according to claim 6, wherein said valve comprises a piston-cylinder unit, and a housing of the cylinder-piston unit (16) is formed integrally with the wall portion or the pipe section (27).

9. Turbine handpiece according to claim 1, wherein said handpiece comprises a head piece (3) and a grip sleeve (32) which are releasably connected with each other through a plug-in connection (31).

10. Turbine handpiece according to claim 9, wherein the connection between said headpiece and grip sleeve includes an open end to facilitate access to and mounting of said valve (12).

* * * * *